(12) United States Patent
Scherrer et al.

(10) Patent No.: US 10,329,317 B2
(45) Date of Patent: Jun. 25, 2019

(54) QUINOLINE DERIVATIVE FOR USE IN THE TREATMENT AND PREVENTION OF VIRAL INFECTIONS

(71) Applicants: ABIVAX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

(72) Inventors: Didier Scherrer, Castelnau le Lez (FR); Aude Garcel, Le Cres (FR); Noelie Campos, Le Cres (FR); Jamal Tazi, Clapiers (FR); Audrey Vautrin, Castelnau le Lez (FR); Florence Mahuteau, Saint Remy les Chevreuses (FR); Romain Najman, L'Hay-les-Roses (FR); Pauline Fornarelli, Villebon sur Yvette (FR)

(73) Assignees: ABIV AX, Paris (FR); CENTRE NATIONAL DE LA RECHERCHE SCIENTIFIQUE, Paris (FR); INSTITUT CURIE, Paris (FR); UNIVERSITE DE MONTPELLIER, Montpellier (FR)

( * ) Notice: Subject to any disclaimer, the term of this patent is extended or adjusted under 35 U.S.C. 154(b) by 0 days.

(21) Appl. No.: 15/552,587

(22) PCT Filed: Feb. 19, 2016

(86) PCT No.: PCT/EP2016/053532
§ 371 (c)(1),
(2) Date: Aug. 22, 2017

(87) PCT Pub. No.: WO2016/135052
PCT Pub. Date: Sep. 1, 2016

(65) Prior Publication Data
US 2018/0030078 A1 Feb. 1, 2018

(30) Foreign Application Priority Data
Feb. 23, 2015 (EP) .................................. 15305274

(51) Int. Cl.
*C07H 17/02* (2006.01)
*C07D 405/12* (2006.01)
(52) U.S. Cl.
CPC ........... *C07H 17/02* (2013.01); *C07D 405/12* (2013.01)
(58) Field of Classification Search
None
See application file for complete search history.

(56) References Cited

U.S. PATENT DOCUMENTS 4,434,290 A   2/1984 Bisagni et al.

FOREIGN PATENT DOCUMENTS

| | | |
|---|---|---|
| EP | 2974729 A1 | 1/2016 |
| EP | 2975034 A1 | 1/2016 |
| FR | 2436786 A1 | 4/1980 |
| FR | 2627493 A1 | 8/1989 |
| FR | 2645861 A1 | 10/1990 |
| WO | 2005/023255 A2 | 3/2005 |
| WO | 2010/143169 A2 | 12/2010 |
| WO | 2012/080953 A1 | 6/2012 |
| WO | 2015/001518 A1 | 1/2015 |

OTHER PUBLICATIONS

International Search Report for PCT/EP2016/053532 dated May 6, 2016 (4 pages).
Written Opinion for PCT/EP2016/053532 dated May 6, 2016 (5 pages).
Bakkour et al., "Small-Molecule Inhibition of HIV pre-mRNA Splicing as a Novel Antiretroviral Therapy to Overcome Drug Resistance", PLoS Pathogens, Oct. 2007, vol. 3, No. 10, pp. 1530-1539.
Bllodeau et al., "Potent N-(1,3-Thiazol-2-yl) pyridin-2-amine Vascular Endothelial Growth Factor Receptor Tyrosine Kinase Inhibitors with Excellent Pharmacokinetics and Low Affinity for the hERG Ion Channel", Journal of Medicinal Chemistry, 2004, vol. 47, No. 25, pp. 6363-6372.
Iyidogan et al., "Current Perspectives on HIV-1 Antiretroviral Drug Resistance", Viruses, 2014, vol. 6, No. 10, pp. 4095-4139.

(Continued)

*Primary Examiner* — Traviss C McIntosh, III
(74) *Attorney, Agent, or Firm* — Oliff PLC

(57) ABSTRACT

The present invention relates to a quinoline derivative of formula (1) or one of its pharmaceutically acceptable salts. The present invention further relates to said quinoline derivative for medicament and for use in the treatment or prevention of a viral or retroviral infection and in particular AIDS or an AIDS-related condition or Human Immunodeficiency virus (HIV). The present invention also relates to a pharmaceutical composition comprising said quinoline derivative and to the process for preparing it as to a novel intermediate compound.

(1)

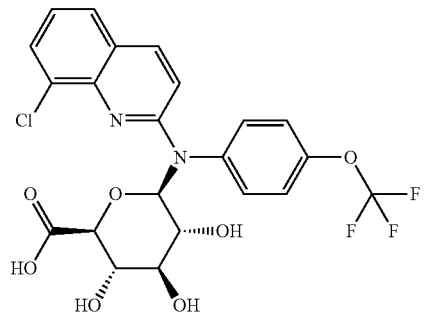

10 Claims, 6 Drawing Sheets

(56) References Cited

OTHER PUBLICATIONS

MacLean et al., "Effective of Collision Energy Optimization on the Measurement of Peptides by Selected Reaction Monitoring (SRM) Mass Spectrometry", Analytical Chemistry, 2010, vol. 82, No, 24, pp. 10116-10124.

Mazza et al., "Crystal Structure of the Human Nuclear Cap Binding Complex", Molecular Cell, Aug. 2001, vol. 8, No. 2, pp. 383-396.

Mazza et al., "Large-scale Induced fit recognition of an m7GpppG cap analogue by the human nuclear cap-binding complex", The European Molecular Biology Organization Journal, 2002, vol. 21, No. 20, pp. 5548-5557.

Olsen et al., "Parts per Million Mass Accuracy on an Orbitrap Mass Spectrometer via Lock Mass injection into a C-trap*", Molecular & Cellular Proteomics, 2005, vol. 4, No. 12, pp. 2010-2021.

Schirle et al., "Mass Spectrometry-Based Proteomics in Preclinical Drug Discovery", Chemistry & Biology, Jan. 2012, vol. 19, No. 1, pp. 72-84.

Shevchenko et al., "Mass Spectrometric Sequencing of Proteins from Silver-Stained Polyacrylamide Gels", Analytical Chemistry, Mar. 1996, vol. 68, No. 5, pp. 850-858.

Wang et al., "Resveratrol Glucuronides as the Metabolites of Resveratrol in Humans: Characterization, Synthesis, and Anti-HIV Activity",Journal of Pharmaceutical Sciences, 2004, vol. 93, No. 10, pp. 2448-2457.

Williams et al., "Drug-Drug Interactions for UDP-Glucuronosyltransferase Substrates: A Pharmacokinetic Explanation for Typically Observed Low Exposure (AUC/AUC) Rations", Drug Metabolism and Disposition, 2004, vol. 32, No. 11, pp. 1201-1363.

Worch et al., "Specificity of recognition of mRNA 5' cap by human nuclear cap-binding complex", RNA, 2005, vol. 11, No. 9, pp. 1355-1363.

Bollenback et al., "The Synthesis of Aryl-D-glucopyranosiduronic Acids", Journal of the American Chemical Society, Jun. 1955, vol. 77 No. 12, pp. 3310-3315.

QUINOLINE DERIVATIVE FOR USE IN THE TREATMENT AND PREVENTION OF VIRAL INFECTIONS

FIELD OF THE INVENTION

The present invention relates to a new quinoline derivative for use in the treatment or prevention of viral infections and virus-related conditions, in particular HIV infections.

BACKGROUND OF THE INVENTION

The invention relates to a novel compound for the preparation of compositions useful for the treatment of diseases resulting from changes in splicing processes.

Certain indole derivative compounds such as ellipticine derivatives and aza-ellipticine derivatives are already known as intercalating molecules for correcting dysfunctions in gene expression, notably in DNA replication. They have been more specifically described for treating diseases such as cancer, leukemia or AIDS (see in particular patents FR 2 627 493, FR 2 645 861, FR 2 436 786).

One of the strategies to combat viral infections and/or virus-related conditions, and more particularly HIV/AIDS, is to use derivatives able to selectively inhibit certain splicing defects.

The International application WO05023255, filed by the Applicant, disclosed the use of indole derivatives to treat diseases related to the pre-messenger RNA splicing process in the cell.

It was then shown that certain indole derivatives prove particularly effective in treating metastatic cancer and in treating AIDS (BAKKOUR et al., *PLoS Pathogens*, vol. 3, p. 1530-1539, 2007).

However there remains a need for novel compounds for treating or preventing a viral infection or a virus-related condition in a patient, including HIV and AIDS.

Among virus-related conditions, AIDS has developed into a worldwide pandemic. More than 30 million people are infected with Human Immunodeficiency Virus (HIV). Current therapies have succeeded in controlling the disease but long-term use of Anti-Retroviral Therapy (ART) is limited by issues of drug resistance and side effects.

Alternatives to ART, including for example a combination 3TC-Tenofovir-Raltegravir and AZT (HAART), have thus been proposed.

Access to Highly Active Anti-Retroviral Therapy (HAART), based upon the combination of HIV protease and reverse transcriptase inhibitors, has dramatically changed the prognosis of HIV infection. As a result, HIV is considered as a chronic disease in developed countries. However, long-term use of HAART is limited by issues of drug resistance and side effects.

There is a continuing need for new drugs, in particular those acting through new and as yet unexplored mechanisms of action to treat and/or prevent viral infections and virus-related conditions, and more particularly to achieve HIV infection control or cure.

There is also a need for drugs, and compositions thereof, which are suitable for lower frequency administration and/or which are characterized by long-term efficiency and/or sustained drug exposure.

Recently some quinoline derivatives have been described in the following patent applications: WO2010/143169, WO2012080953, EP14306164, and EP14306166 useful in the treatment of HIV/AIDS or of inflammatory diseases.

SUMMARY OF THE INVENTION

The present invention relates to a compound of formula (1)

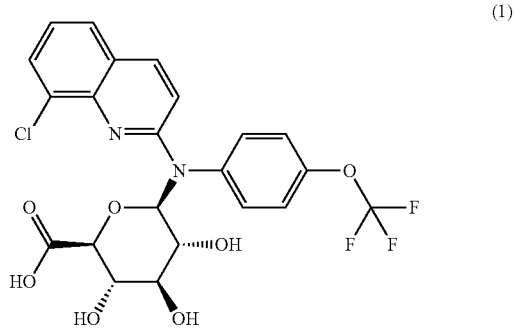 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

(1)

or one of its pharmaceutically acceptable salts and to the pharmaceutical composition comprising it. This compound can be used in the treatment or prevention of viral or retroviral infection and virus-related conditions, in particular AIDS or an AIDS-related condition or Human Immunodeficiency virus (HIV).

The invention further relates to a compound of formula (1), or one of its pharmaceutically acceptable salts, in a medicament.

The invention also relates to a process for preparing the compound of formula (1) and also to one intermediate compound in said process.

The invention further relates to the intermediate compound of formula (4)

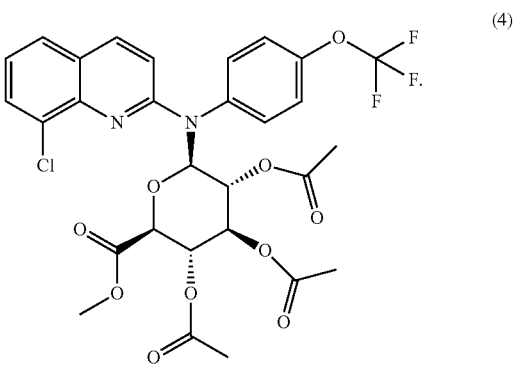 [SMILES: COC(=O)[C@H]1O[C@@H](N(c2ccc(OC(F)(F)F)cc2)c2ccc3cccc(Cl)c3n2)[C@H](OC(C)=O)[C@@H](OC(C)=O)[C@@H]1OC(C)=O]

(4)

Figure 1A:
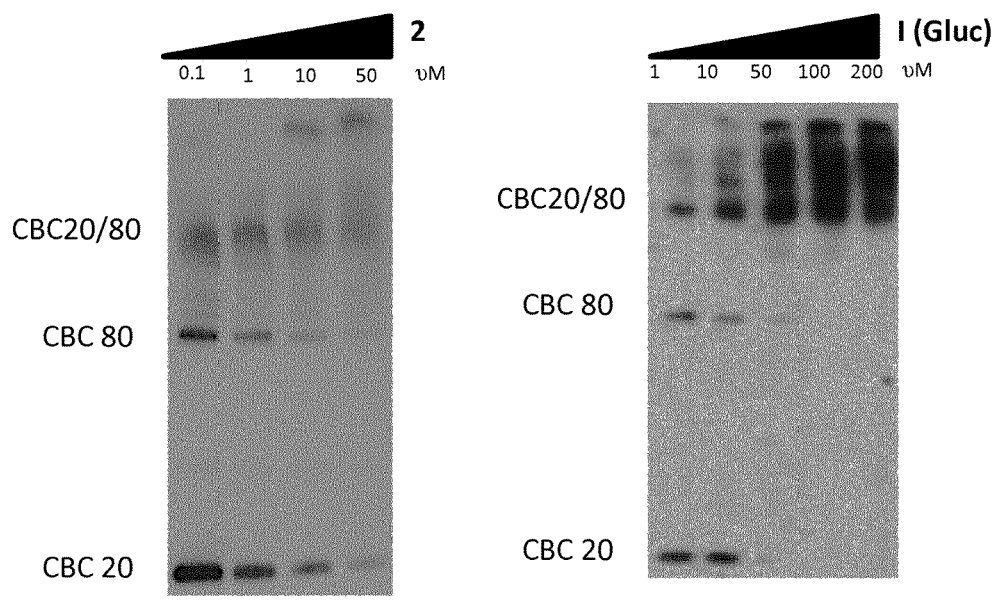
FIG. 1A. Compounds 1 and 2 interact with the CBC complex. Purified recombinant CBP20 and CBP80 proteins were incubated with increasing concentrations of Compound 2 (left panel) or Compound 1 (right panel, Gluc) and treated during 30 min (Compound 1) or 15 min (Compound 2) with UV light. The proteins were revealed by Western Blotting using CBP20 and CBP80 antibodies. Left panel: from left to right, incubation with 0.1 (lane 1), 1 (lane 2), 10 (lane 3) and 50 µM (lane 4) of Compound 1. Right panel.

from left to right, incubation with 1 (lane 1), 10 (lane 2), 50 (lane 3), 100 µM (lane 4) and 200 µM (lane 5) of Compound 1.

Figure 1B:
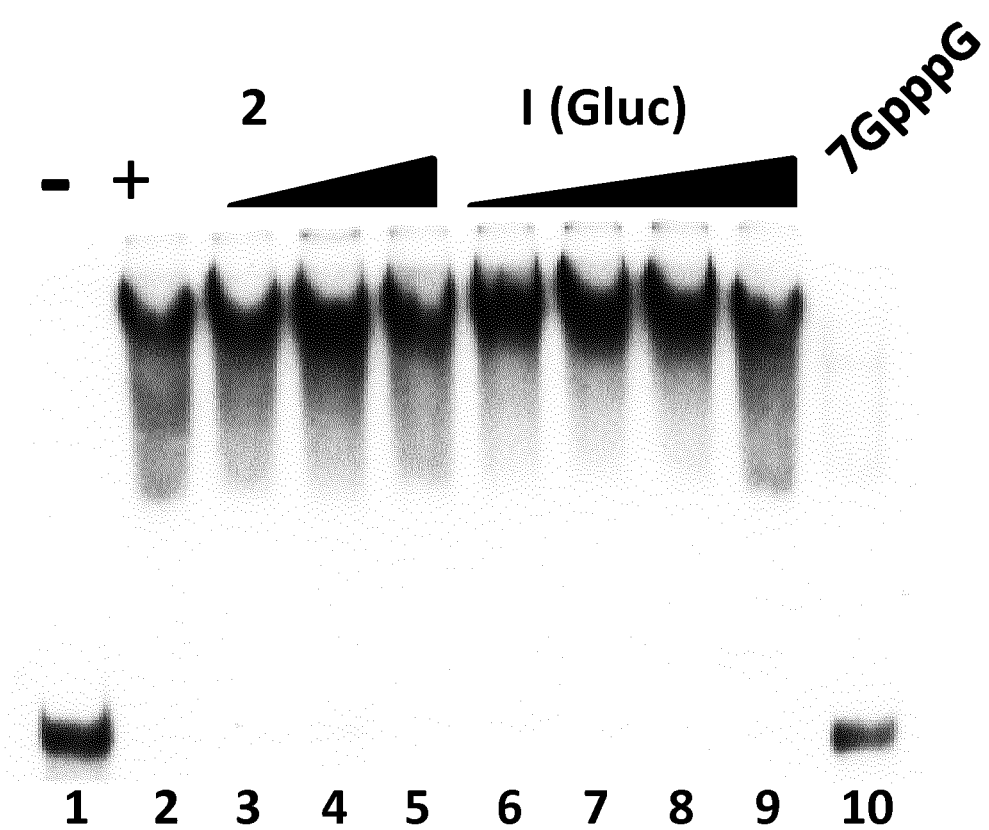

FIG. 1B. Unlike m7GpppG cap structure, Compounds 1 and 2 do not Interfere with the binding of capped RNA to the CBC complex. Recombinant human CBC was incubated with a capped RNA substrate and analyzed by native gel electrophoresis in order to resolve the different RNA and RNA-protein complexes: free RNA (lane 1), and CBC-RNA complexes (lanes 2-10) in the presence of 12 mM of m7GppG (lanes 10) or 5 µM, 10 µM or 50 µM of Compound 2 (lanes 2-5, respectively) and 5 µM, 10 µM, 50 µM or 100 µM of Compound 1 (lanes 6-9, respectively).

Figure 2A:
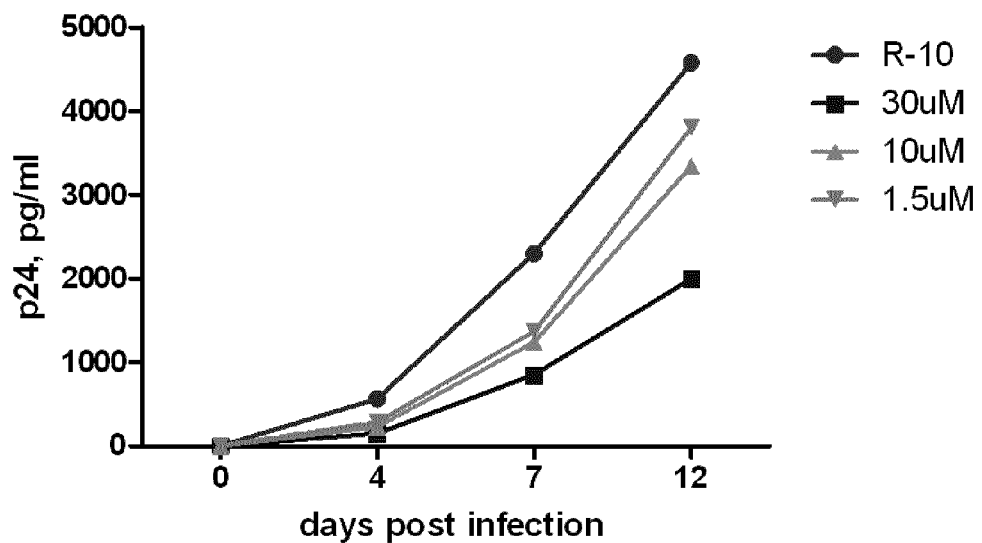
Figure 2B:
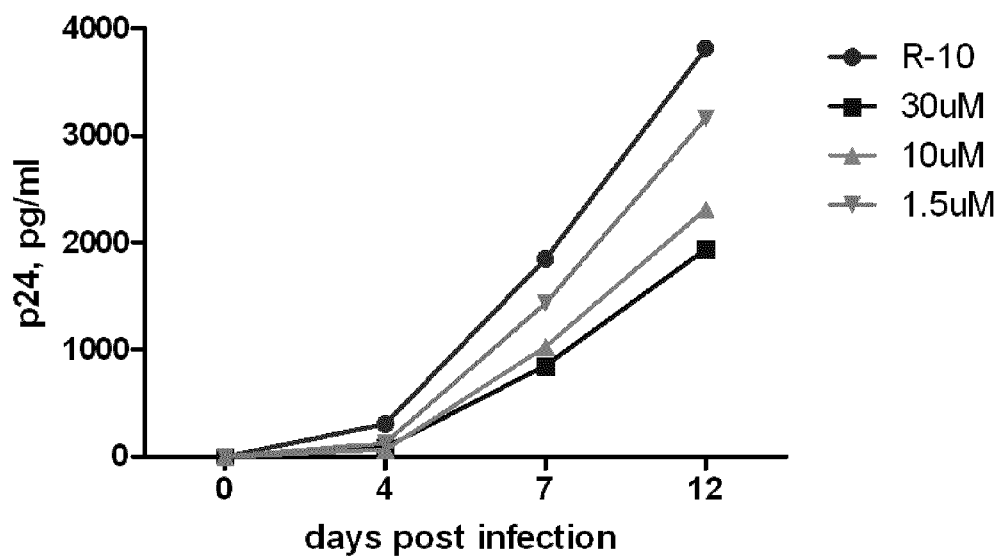
Figure 2C:
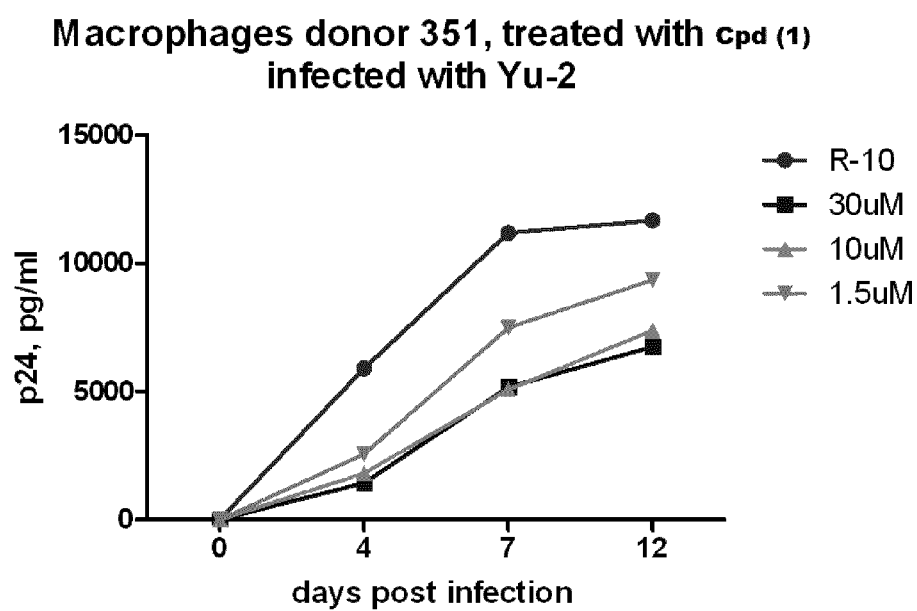
Figure 2D:
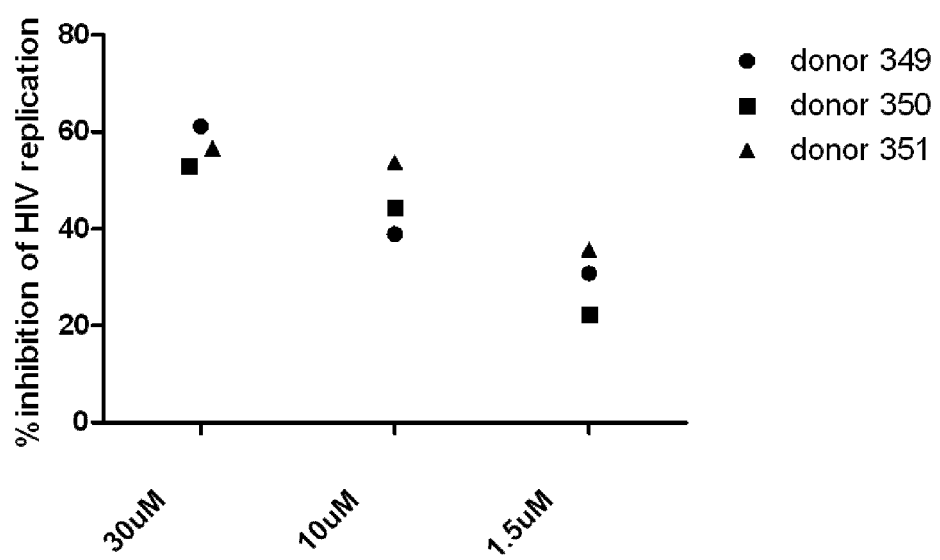

FIG. 2A-D. Potency of Compound 1 to inhibit HIV-1 production in macrophages-infected cells. HIV-1 strain YU2 was used to infect monocyte derived-macrophages from three different donors (donors 349, 350 and 351; respectively FIGS. 2A, 2B, and 2C panel) in the presence of increasing concentrations of the (glucuronidated) Compound 1, at 1.5 µM, 10 µM and 30 µM. The viral capsid protein p24 antigen was quantitated using standard ELISA protocol (expressed in pg/mL in y-axis). R-10 corresponds to untreated cells. FIG. 2D: the % of inhibition of HIV replication is further assessed at three concentrations, and compared for each concentration between donors.

DETAILED DESCRIPTION OF THE INVENTION

The present invention has for purpose to meet the aforementioned needs.

The present invention relates to a compound of formula (1)

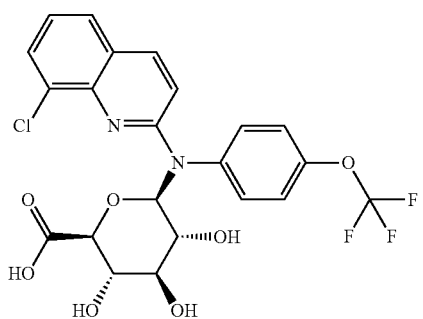

(1)

or one of its pharmaceutically acceptable salts. This compound is also referred herein as the Compound 1, cpd (1) or Glue.

Said compound may exist in the form of a base or an addition salt with an acid, particularly a pharmaceutically acceptable acid.

Suitable physiologically acceptable acid addition salts of compound of formula (1) include hydrobromide, tartrate, citrate, trifluoroacetate, ascorbate, hydrochloride, tartrate, triflate, maleate, mesylate, formate, acetate and fumarate.

The compound of formula (1) and or salts thereof may form solvates or hydrates and the invention includes all such solvates and hydrates.

The terms "hydrates" and "solvates" simply mean that the compound of formula (1) according to the invention can be in the form of a hydrate or solvate, i.e. combined or associated with one or more water or solvent molecules.

The compound of formula (1) as depicted above is an unexpected human liver metabolite, and more particularly a N-glucuronide metabolite, of the compound of formula (2)

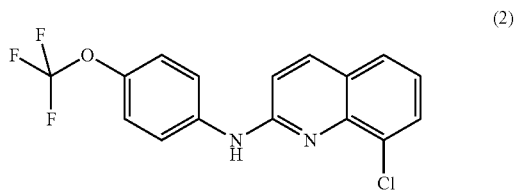 [SMILES: FC(F)(F)Oc1ccc(Nc2ccc3cccc(Cl)c3n2)cc1]

(2)

which as such is an active compound for treating a viral infection or a virus-related condition in a patient, in particular an Human Immunodeficiency Virus (HIV) infection, and a virus-related condition such as AIDS, as disclosed in WO2010/143169.

Compound (1) has the following chemical name: N-β-glucuronide of 8-chloro-N-(4-(trifluoromethoxy)phenyl) quinolin-2-amine.

Compound (1) can be further characterized by a sustained drug exposure, which translates into a remarkably long elimination half life of about 100 h (ranging from about 90 to about 110 h). This is surprising, because glucuronidation has also been reported in the Art as a clearance mechanism for many drugs (see for instance Williams et al.; Drug Metabolism and Disposition; Vol. 32, No. 11; 2004).

High clearance is generally associated with short elimination half-life and short drug exposure. On the contrary, low clearance is generally associated with long elimination half-life and sustained drug exposure.

This compound of formula (2) is also referred herein as the Compound 2.

Thus, according to another aspect, a subject-matter of the present invention relates to a compound of formula (1) or its pharmaceutically acceptable salts, for use as a medicament.

According to another of its objects, the invention relates to a pharmaceutical composition comprising a compound of formula (1) or its pharmaceutically acceptable salts and at least one pharmaceutically acceptable excipient, and to the medicament comprising the compound of formula (1) or one of its pharmaceutically acceptable salts.

The compound of formula (1), or one of its pharmaceutically acceptable salts, can be used in the treatment or prevention of viral or retroviral infections and virus-related conditions, in particular AIDS or an AIDS-related condition or Human Immunodeficiency virus (HIV). More specifically, it is shown herein that such compound (i) reduces HIV-1 viral load in HIV-infected mammals and (ii) maintains or restores a high level of CD4+ cell count in HIV-infected mammals.

The inventors further provide evidence that this compound (1) has long-term treatment effect in patients, and is suitable for treating or preventing a viral infection or a virus-related condition in a patient.

The inventors further provide evidence that said compound (1) is particularly suitable as a medicament, due to its improved pharmacokinetic properties.

The compound of formula (1) which is suitable for the invention may be prepared according to Scheme I below:

Scheme 1

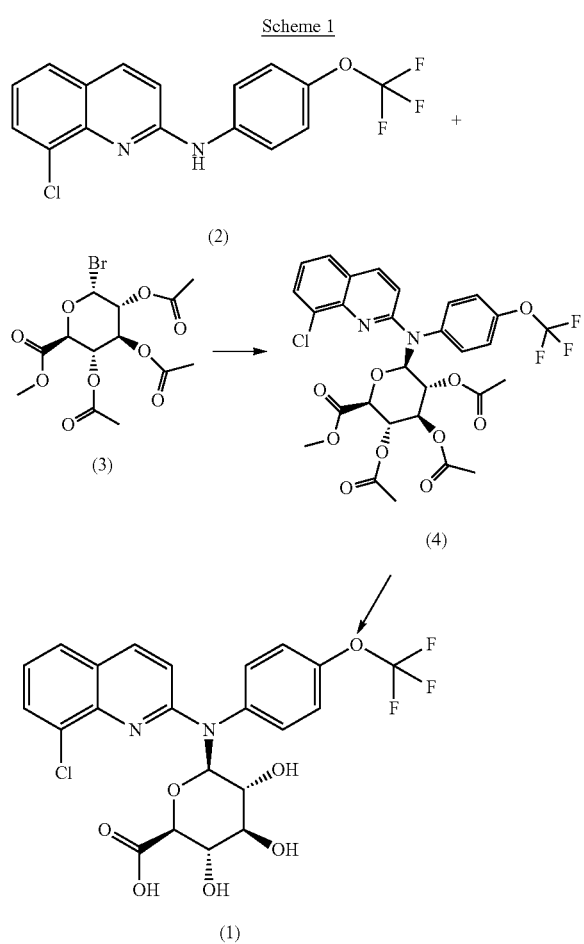

Compound (2) may be synthetized according to the process as described in WO2010/143169.

Compound (3) may be synthetized in two steps according to scheme 2 below

Scheme 2

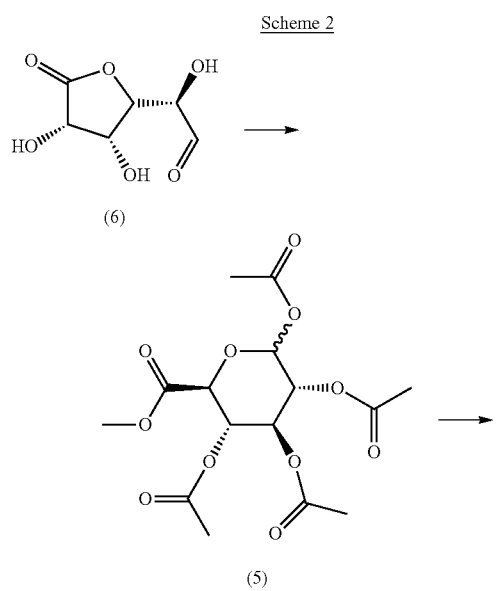

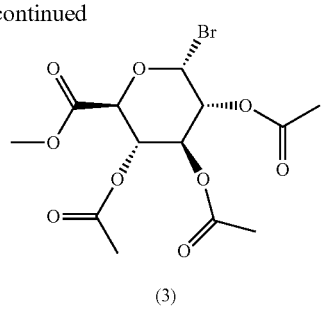

Compound (6), which is commercially available, may be placed in anhydrous methanol in presence of a metal, such as sodium, at a temperature ranging from −20° C. to 10° C., for example at 0° C., for a time ranging from 1 to 7 hours, for example during 5 hours. The reaction mixture can be allowed to be treated with a resin, for example with Amberlite® IR-120 (Ir) resin, for example until pH reaches 3, and then filtered. The gum as obtained after filtration and removal of the solvent can be dissolved in acetic anhydride in the presence of perchloric acid. The reaction mixture may be stirred for a time, for example ranging from 1 to 16 hours, in particular during 12 hours under inert atmosphere of gas, then washed and dried to afford compound (5). Said stage procedure conditions more particularly described in Bollenback, G. N., Long, J. W., Benjamin, D. G., Lindquist, J. A., J. Am. Chem. Soc., 1955, 77, 3310. An illustration of said procedure stage is given in example 1 herein after.

To compound (5) as obtained above, hydrobromic acid in acetic acid may be added under an inert atmosphere of gas, for example argon or nitrogen, at a temperature ranging from −20° C. to 10° C., for example at 0° C., and stirred for a time, for example ranging from 1 to 5 days, in particular in a dessicator, for example during 2 days at 4° C. The obtained mixture can be diluted with ethyl acetate and poured into ice, then washed, dried and optionally purified to afford compound (3). An illustration of said procedure stage is given in example 1 herein after.

Compound (2) can be activated by placing it in a solvent such as anhydrous toluene in presence of a heavy metal salt such as cadmium salt, and for example cadmium carbonate. The reaction between compounds (2) and (3) may be performed according to a Koenigs-Knorr synthesis, which is well known to the man skilled in the art, suitably in a solvent such as nitromethane, typically at the reflux temperature of the solvent. After reflux, and optionally filtration and/or washing and/or purification steps, compound (4) is obtained. Example 2 herein after illustrates this stage.

Compound (4) may be thereafter treated by using hydroperoxide salts, for example by addition of hydrogen peroxide to a lithium hydroxide monohydrate in water to obtain a solution of lithium hydroperoxide. Compound (4) may thus be placed in a solvent such as tetrahydrofurane or dioxan in presence of the previous obtained solution, and be stirred for example during 0.5 to 1.5 hours. The resulting precipitate can be purified to afford compound (1). Example 3 herein after illustrates this stage of the synthesis.

Therefore, the invention also relates to the process for preparing the compound of formula (1), comprising the step of treating the compound (4) in a solution of lithium hydroperoxide, for example in a solvent such as tetrahydrofuran or dioxin, optionally preceded by a step of obtaining a compound (4) consisting in reacting a compound of formula (2) with a compound of formula (3) as defined above, in the presence of a heavy metal salt, such as cadmium salt, for example cadmium carbonate, in particular in a solvent such as nitromethane, typically at the reflux temperature of the solvent.

The invention also extends to the compound of formula (4), which is an intermediate compound:

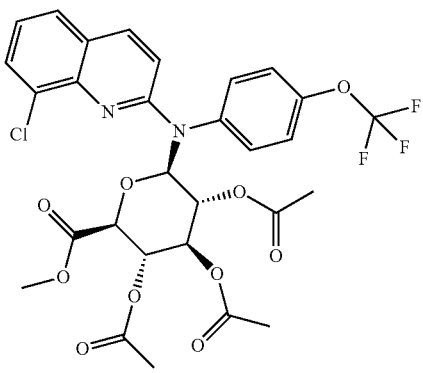

(4)

or one of its pharmaceutically acceptable salts.

Viruses

The quinoline derivative of the present invention is suitable for treating or preventing viral infections, and in particular HIV infection or a virus-related condition and in particular AIDS.

In a non-limitative manner, examples of viruses which are considered by the invention include enveloped and naked viruses, which includes DNA viruses, RNA viruses and retroviruses, which includes dsDNA viruses, ssDNA viruses, dsRNA viruses, (+)ssRNA viruses, (−)ssRNA viruses, ssRNA-RT viruses and dsDNA-RT viruses, which includes oncoviruses, lentiviruses and spumaviruses.

The oncoviruses are thus termed because they can be associated with cancers and malignant infections. There may be mentioned, for example, leukemogenic viruses (such as the avian leukemia virus (ALV), the murine leukemia virus (MULV), also called Moloney virus, the feline leukemia virus (FELV), human leukemia viruses (HTLV) such as HTLV1 and HTLV2, the simian leukemia virus or STLV, the bovine leukemia virus or BLV, the primate type D oncoviruses, the type B oncoviruses which are inducers of mammary tumors, or oncoviruses which cause a rapid cancer (such as the Rous sarcoma virus or RSV).

The spumaviruses manifest fairly low specificity for a given cell type or a given species, and they are sometimes associated with immunosuppressive phenomena; that is the case, for example, for the simian foamy virus (or SFV).

The lentiviruses, such as HIV, are thus named because they are responsible for slow-progressing pathological conditions which very frequently involve immunosuppressive phenomena, including AIDS.

Viruses, and in particular retroviruses such as HIV, HTLV-I and HTLV-II, are known to rely upon RNA splicing and splicing regulation in order to spread and disseminate within cells and tissues of an infected individual. Other viruses of interest are viruses pathogenic for human, including but not limited to HSV family viruses (including 1, 2, 6), CMV, VZV, HBV, HCV, Hepatitis E virus, Papilloma viruses, RSV, Rhino viruses, influenza viruses, adenoviruses, EBV, Ebola, Nipah viruses, and other arboviruses, Dengue, Chikungunya, West Nile viruses, Rift valley virus, Japanese encephalitis virus, SRAS other coronaviruses, parvovirus, enteroviruses.

Other viruses of interest are viruses pathogenic for animals, including, but not limited to, influenza, FLV, pestivirus, Hantavirus, and lyssavirus.

In particular, viruses and virus-related conditions which are considered include viruses of which viral replication requires RNA splicing, and/or viral RNA export from the nucleus to the cytoplasm.

Examples of viruses include latent viruses and/or retroviruses and/or viruses which are associated with chronic viral infections.

Viruses which are more particularly considered are RNA viruses and retroviruses, including lentiviruses, and preferably HIV. Accordingly, virus-related conditions which are more particularly considered are associated with a RNA virus or a retrovirus, and preferably HIV.

HIV may include HIV-I, HIV-2 and all subtypes thereof, which includes HIV-I strains belonging to the HIV-I B subtype, HIV-I C subtype, and HIV-I recombinants. Examples include HIV-I strains selected from Ad8, AdaM, Isolate B, Isolate C, CRF01, CRF02 and CRF06.

According to a particular embodiment, viruses may include HIV-strains which have developed resistances for current treatments.

According to a preferred embodiment, the virus-related condition is AIDS.

Therapeutic Use

The above-mentioned compound is particularly suitable for treating or preventing a virus infection, and more particularly a HIV-infection or a HIV-related condition. Also, the above-mentioned compound is particularly suitable for treating a latent HIV infection in an individual, for eradicating an HIV-infection or a HIV-related condition in an individual, including eradicating HIV and/or for use as a cure for HIV and HIV-related conditions.

The invention also relates to the use of a compound of formula (1) for the preparation of a composition, such as a medicament, for treating or preventing a viral infection or a virus-related condition, and more particularly AIDS, an AIDS-related condition or HIV.

The invention further relates to a method for treating or preventing a viral infection or a virus-related condition, and in particular for treating or preventing a HIV infection in a patient, consisting in administering to said patient in need thereof, an effective amount of a quinoline derivative of formula (1) as described above or a pharmaceutical composition containing it.

Moreover the invention relates to a quinoline derivative of formula (1) as defined herein above, or anyone of its pharmaceutically acceptable salts, for use for decreasing the viral load and/or for increasing or restoring the level of CD4+ cell count in an HIV-positive patient.

In particular the invention relates to a quinoline derivative of formula (1) as defined herein above, or anyone of its pharmaceutically acceptable salts, for use for treating or preventing a HIV infection or a HIV-related condition in a patient; and then terminating said treatment when: the viral load is low or undetectable; and/or the level of CD4+ cell count is maintained or restored.

For reference, and as further described herebelow, a low viral load is usually below 500 copies/mL of plasma and an undetectable viral load is usually below 40 copies/mL.

For reference, and as further described herebelow, a restored CD4+ cell count may correspond to a physiological (or "normal") CD4+ cell count, which is generally equal or superior to 500 CD4+ cells/mm$^3$ of plasma, and which generally varies between 500 and 1500 CD4+ cells/mm$^3$ of plasma, though it may be lower for some individuals.

Alternatively a restored CD4+ cell count may correspond to an increase of the CD4+ cell count, compared to the CD4+ cell count in said patient prior to said treatment.

The invention also relates to a quinoline derivative of formula (1) as defined herein above, or anyone of its pharmaceutically acceptable salts, for use for treating or preventing a HIV infection or a HIV-related condition in a patient, for which an ineffectiveness in prior anti-retroviral treatment, or a decline in prior anti-retroviral treatment effectiveness has been stated.

The invention also relates to a quinoline derivative of formula (1) as defined herein above, or anyone of its pharmaceutically acceptable salts, for use for treating or preventing a HIV infection or a HIV-related condition in a patient, wherein the patient is infected by a drug-resistant HIV strain.

As used herein, "patient" may extend to humans or mammals, such as cats or dogs. As used herein, "preventing" also encompasses "reducing the likelihood of occurrence" or "reducing the likelihood of reoccurrence".

It is shown in the examples herein that the quinoline derivative of formula (1) reduces HIV replication in HIVs-infected mammals.

According to a particular embodiment, the inventors provide evidence that said quinoline derivative of formula (1) has long-term treatment effect and present a significant reduced rebound, in particular as compared to classical anti-retroviral drugs.

Without wishing to be bound by any particular theory, the inventors believe that the quinoline derivative of the invention is able to modulate the activity of the viral protein Rev, and in particular modulate the Rev-mediated export of viral RNAs.

Without wishing to be bound by any particular theory, the inventors also believe that such quinoline derivative has unexpected properties in targeting latent HIV reservoirs.

The reasons which explain the rebound of viral infections in previously-treated patients include:
(i) the fact that many viruses, including retroviruses such as HIV or DNA viruses of the Herpesviridae family, are characterized by viral latency, which is the ability of a virus to lie dormant within a cell, thus defining the lysogenic part of the viral life cycle. Latency is the phase of the viral replication cycle in which, after initial infection, proliferation of virus particles ceases without full eradication. The phenomenon of viral latency is associated to the appearance of so-called "reservoirs" within the host, which are generally difficult to reach, and which are also one of the main reasons of the difficulty to provide a cure for HIV;
(ii) the emergence of drug-resistant strains, especially for viral infections requiring a long-term treatment. The probability of appearance of mutant strains is particularly important for retroviruses, including HIV. Indeed, resistance to anti-HIV drugs can be explained at the biological level as follows. As a retrovirus, HIV uses the enzyme reverse transcriptase to synthesize DNA from its RNA genome and lacks a mechanism for correcting errors made while reproducing its genome. As a result, HIV replicates its genome with the highest known mutation rate of any 'living' organism. This creates an ideal situation for natural selection to act on the HIV population, as genetic variation is the raw material for natural selection.

These mutations accumulate over generations and in populations, resulting in the great genetic variation within populations of HIV, and an increased probability of a virion developing an evolutionary selective advantage over other virions. Natural selection then acts on HIV by selecting for virions with higher fitness, as all others are eventually killed off by drug treatments. The virions that are able to escape the harmful effects of the drug then create an entirely new, drug resistant population.

The consequence of a decline in a prior treatment effectiveness is that the virions reproduce until the patient has an increased, detectable population of viruses as large as they originally did as large as before treatment reduced these numbers. This creates a cycle in which patients, especially HIV-positive patients, first experience success with treatment, as:
  their viral load is controlled or even decreased;
  their level of CD4+ cell count is maintained or even restored; and/or
  the clinical signs which are generally associated with a virus-related condition such as AIDS are stabilized or even disappear. The clinical signs of AIDS vary, depending on the phase of infection.

Then, over time, those patients may experience a decline in treatment effectiveness as the virus develops resistance and rebuilds its population of virus particles.

In particular, this phenomenon is enhanced for anti-HIV therapies, at least for three reasons which include:
(i) the fact that HIV is a retrovirus, and the appearance of novel mutant strains is particularly important for this class of viruses, as stated previously;
(ii) the fact that HIV has the ability to enter into a latent phase and thus form "latent" reservoirs which are not efficiently targeted by the currently available treatments;
(iii) the fact that currently available treatments also tend to select HIV mutant strains over time, which in the long-term has a major role in the emergence of drug resistance.

As used herein, an "anti-HIV agent" means a classical drug, or combination of drugs, administered to fight HIV infection. It may in particular be ART (Antiretroviral Therapy) or HAART (Highly Active Antiretroviral Therapy).

ART and HAART generally relate to combinations of two, three or more antiretroviral medicines. Such antiretroviral medicines encompass:
(i) nucleoside/nucleotide reverse transcriptase inhibitors also called nucleoside analogs, such as abacavir, emtricitabine, and tenofovir;
(ii) non-nucleoside reverse transcriptase inhibitors (NNRTIs), such as efavirenz, etravirine, and nevirapine;
(iii) protease inhibitors (PIs), such as atazanavir, darunavir, and ritonavir;
(iv) entry inhibitors, such as enfuvirtide and maraviroc;
(v) integrase inhibitors, such as dolutegravir and raltegravir.

As used herein, an "anti-HIV treatment" encompasses in particular:
  the action of an anti HIV-agent in reducing the viral load during a determined period, but not necessarily showing a long-lasting lowering of said viral load after termination of said treatment; and/or
  the action of an anti HIV-agent in increasing the level of CD4+ cell count in HIV-infected patients.

According to one embodiment of the invention, the present invention concerns a quinoline derivative of formula (1) as described above, or one of its pharmaceutically acceptable salts, for use in the treatment or prevention of viral infection or a virus-related condition in patients, in particular HIV infection or AIDS, or and more particularly where the use maintains a low viral load after treatment termination.

According to said aspect, the invention relates to a quinoline derivative of formula (1) as defined herein, or one of its pharmaceutically acceptable salts, for use in the treatment or prevention of a virus infection or virus-related condition in patient, in particular a HIV infection or a HIV-related condition, wherein: a low or undetectable viral load is maintained; and/or a CD4+ cell count is stable or increased; after treatment termination.

Still, according to said aspect, the invention relates to a quinoline derivative of formula (1) as defined herein, or one of its pharmaceutically acceptable salts, for use for treating or preventing a virus infection or virus-related condition in patient, in particular a HIV infection or a HIV-related condition, and then terminating said treatment, wherein: a low or undetectable viral load is maintained; and/or a CD4+ cell count is stable or increased; after treatment termination.

In the framework of the present invention "maintaining a low viral load after treatment termination" means maintaining a viral under the detectable level or having a time to rebound increase by at least 2 weeks compared to ART and HAART.

As used herein the "viral load" also refers to the "viral titer", and it can be determined directly or indirectly. For reference, the viral load generally refers to:
- the number of copies of virus RNA or DNA per mL of a plasma sample;
- the number of virus particles per mL of a plasma sample; and/or
- the activity of a virus-related protein in a plasma sample.

As used herein the "HIV viral load" also refers to the "HIV viral titer", and it can be determined directly or indirectly. For reference, the viral load generally refers to:
- the number of copies of HIV RNA per mL of a plasma sample; and/or
- the number of HIV particles per mL of a plasma sample; and/or
- the activity of a HIV-related protein in a plasma sample, which may for example include determining the reverse transcriptase (RT) activity in said plasma sample.

For reference, methods for determining the HIV viral load in a sample include:
- determining the number of copies of HIV RNA per mL of sample; and/or
- determining the number of HIV particles per mL of sample; and/or
- determining the activity of a HIV-related protein in the sample.

Preferably, the "HIV viral load" refers to the number of copies of HIV RNA per mL of a plasma sample.

A low viral load is usually below 500 copies/mL of plasma; which includes between 20 and 500 copies/mL of plasma, or 40 to 500 copies/mL of plasma, depending on the type and sensitivity of the test that is used. This result indicates that HIV is not actively reproducing and that the risk of disease progression is low.

A low viral load may consist of a viral load below 500 copies/mL; which includes below 450, 400, 350, 300, 250, 200, 150, 100, 50, 40, 30, 20, 10, 9, 8, 7, 6, 5, 4, 3, 2, and 1 copies/mL of plasma.

An undetectable viral load for routine methods is generally below 40 copies/mL of plasma, which includes 20 copies/mL of plasma, in particular when measured with a method and/or kits selected from: COBAS® AmpliPrep/COBAS® TaqMan® HIV-1 Test and COBAS® AMPLICOR HIV-1 MONITOR Test sold by Roche Molecular Diagnostic or NucliSENS EasyQ®HIV-1 sold by Biomerieux Diagnostics.

More particularly, according to this aspect, the invention relates to doses and regimens of a quinoline derivative of formula (1), or one of its pharmaceutically acceptable salts, in the treatment or prevention of viral or retroviral infection, and in particular of HIV infection, wherein the viral load after treatment termination is maintained low.

In other words, the viral load remains preferably at an undetectable level at least two weeks after the treatment termination, compared to ART or HAART treatment, which includes at least three, four, or five weeks after the treatment termination.

This means that the quinoline derivative of formula (1), or one of its pharmaceutically acceptable salts, presents a surprisingly long-lasting therapeutic effect and absence of resistance.

In particular the elimination half-life has been determined in the examples and is of about 100 h (ranging from about 90 h to about 110 h).

According to a particular embodiment, a quinoline derivative of formula (1) according to the present invention, may be administered at various dosages and regimen and in particular once a day, once every three days, once a week, once every two weeks or once every month, at doses ranging from 25 to 1000 mg, in particular from 25 to 700 mg, for example from 25 to 500 mg, and more particularly from 25 to 300 mg, during the treatment period or as a continuous treatment.

According to one embodiment, the quinoline derivative of formula (1) according to the present invention, may thus be administered at doses ranging from about 50 mg to about 200 mg, about 50 mg to about 300 mg, or about 50 mg to 400 mg.

Due to its long elimination half life, the quinoline derivative can be administered, in particular, once every three days, once every four days, once every five days, once every six days, once every week, once every two weeks or even once every month.

A "continuous treatment" means a long-term treatment which can be implemented with various administration frequencies, such as once every three days, or once a week, or once every two weeks or once every month.

The treatment period, i.e. when the treatment is non continuous, may vary between 2 weeks and 8 weeks, which includes 2, 3, 4, 5, 6, 7 and 8 weeks.

According to another embodiment, the invention relates to a quinoline derivative of formula (1) as defined herein, or one of its pharmaceutically acceptable salts, for use in the treatment or prevention of a virus infection or virus-related condition in patient, in particular a HIV infection or a HIV-related condition, for which a decline in a prior antiviral, or anti-retroviral, treatment effectiveness has been stated.

As used herein "a decline in prior treatment effectiveness has been stated" may be indicative that resistant strains of the virus appear during said prior treatment, such strains not being fought by the anti-HIV agent.

In a non-limitative manner, an ineffectiveness or decline of a prior treatment effectiveness in a patient may occur for instance because:
- the patient is infected with a virus strain, in a particular an HIV strain, of which the replication and/or infectivity was thought to be stabilized or even decreased, but that is not responsive anymore to the treatment, which includes ART and HAART treatment; and/or the patient is infected with a drug-resistant strain.

In particular, the definition encompasses previously treated patients, of which the HIV viral load and/or the level of CD4+ cell count and/or low establishing thereby a reference value, and which upon treatment or after present at least one of the following:

an increase of the HIV viral load; and/or a decrease of the level of CD4+ cell count; and/or wherein the HIV viral load and/or the level of CD4+ cell count is/are established preferably in a plasma sample.

In such cases, the statement of the ineffectiveness or decline of the effectiveness of said prior treatment may be assessed by measuring the viral load which has increased above the detectable level, in particular for several consecutive weeks, for example for at least one or two weeks, in particular at least 3 weeks or 4 weeks of treatment with an anti-retroviral agent, including an anti-HIV agent, the viral load being as defined herein above.

Alternatively, the statement of the ineffectiveness or decline of the effectiveness of said prior treatment may be assessed by measurement of CD4+ cell count in blood plasma which has decreased (again) below 500/mm$^3$, in particular for several consecutive weeks, for example for at least one or two weeks, in particular at least three weeks or four weeks of treatment with an anti-retroviral agent, including an anti-HIV agent, the CD4+ cell count being defined in more details herein above.

For reference, a restored CD4+ cell count may correspond to a physiological (or "normal") CD4+ cell count, which is generally equal or superior to 500 CD4+ cells/mm$^3$ of plasma, which generally varies between 500 and 1500 CD4+ cells/mm$^3$ of plasma, though it may be lower for some individuals.

Accordingly, a low CD4+ cell count includes a CD4+ cell count inferior to 500/mm$^3$ in blood plasma, which includes inferior to 450, 350, 300; 250; 200; 150 and 100/mm$^3$.

According to still another embodiment, the invention relates to a quinoline derivative of formula (1) as defined herein, or one of its pharmaceutically acceptable salts, for use in the treatment or prevention of a virus infection or virus-related condition in patient, in particular a HIV infection or a HIV-related condition, wherein the patient is infected by a drug-resistant strain.

The occurrence of a drug-resistant strain in a patient may be a consequence of either:

selection of a drug-resistant strain from said patient after a prior treatment, as disclosed above; and/or primo-infection of the patient with a drug-resistant strain.

In particular, the above-mentioned methods are suitable for treating or preventing a viral infection or a virus-related condition, for example in Lamivudin (3TC)-resistant, Tenofovir-resistant, Raltegravir-resistant and Azidothymidine (AZT)-resistant individuals.

The quinoline derivative compound according to the invention is also particularly suitable for treating or preventing a viral infection or a virus-related condition in treatment-resistant individuals, including individuals infected with a resistant HIV-strain, including HAART-resistant and ART-resistant individuals.

Because of the broad efficiency of the quinoline derivatives of the invention, it is now possible to provide novel treatment strategies, even for primo-infected patients with otherwise untreatable strains.

As used herein, "HIV drug resistance" relates to the ability of HIV to mutate and reproduce itself in the presence of antiretroviral drugs.

For reference, a "drug-resistant HIV strain" may be determined by measuring the Reverse Transcriptase (RT) activity in human PBMCs infected with the tested strain, and then treated with the compound or combination of compound for which a resistance is suspected.

Accordingly, the patient has not necessarily been treated previously by an anti-viral treatment, including anti-retroviral treatment or even an anti-HIV-treatment different from said quinoline derivative.

Accordingly, the invention further relates to a quinoline derivative of formula (1) as defined above, or anyone of its metabolites, for use in the treatment or prevention of a HIV infection or a HIV-related condition in a patient, wherein: a low or undetectable viral load is maintained and/or a CD4+ cell count is maintained or restored after treatment termination, and for which the patient has not been treated previously by an anti-retroviral treatment, including an anti-HIV treatment.

Accordingly, the invention further relates to a quinoline derivative of formula (1) as defined above, or anyone of its metabolites, for use in the treatment or prevention of a HIV infection or a HIV-related condition in a patient, wherein the patient is infected by a drug-resistant HIV strain and for which the patient has not been treated previously by an anti-retroviral treatment.

Examples of drug-resistant HIV strains are selected from: mutants of the NL4.3 strain, K103N (resistant to Effavirenz), K65R (resistant to Tenofovir and 3TC) and M184V (resistant to 3TC) mutants, HIV-1 B strains and selected from Ad8 and AdaM; and clinical isolates selected from CRF01, CRF02, and CRF06.

Typical resistant strains are more particularly described in Pinar Iyodogan et al. ("Current Perspectives on HIV-1 Antiretroviral Drug Resistance", Viruses 2014, 6, 4095-4139; doi10.3390/4095) and are further described herebelow.

In particular, the virus strain may be a strain resistant to a drug or a treatment comprising the administration of a drug selected from ART and/or HAART treatments, and/or including (i) nucleoside/nucleotide reverse transcriptase inhibitors (NRTIs) also called nucleoside analogs, such as Abacavir, Emtricitabine, and Tenofovir, (ii) non-nucleoside reverse transcriptase inhibitors (NNRTIs), such as Efavirenz, Etravirine, and Nevirapine;

(iii) protease inhibitors (PIs), such as Atazanavir, Darunavir, and Ritonavir;

(iv) entry inhibitors, such as Enfuvirtide and Maraviroc;

(v) integrase inhibitors, such as Dolutegravir and Raltegravir;

and combinations thereof.

Accordingly, a drug-resistant HIV strain encompasses NRTIs, NNRTIs, PIs, entry inhibitors and integrase inhibitors-resistant HIV strains.

Resistant strains are known in the Art and include, in a non-limitative manner, strains bearing a resistance mutation as disclosed in the International Antiviral Society—USA (IAS-USA) and Stanford HIV drug databases.

Typical resistant HIV strains include strains bearing a resistance mutation selected from:

M41; K65; D67; K70; L74; Y115; M184 (including M184 V/I); L210; T215; K219; as major NRTI resistance mutations;

M41; A62; D67; T69; K70; V75; F77; F116; Q151; L210; T215; K219; as multi-NTRI resistance mutations;

V90; A98; L100; K101; K103; V106; V108; E138; V179; Y181; Y188; G190; H221; P225; F227; M230; as major NNRTI resistance mutations;

L10; V11; G16; K20; L24; D30; V32; L33; E34; M36; K43; M46; I47; G48; I50; F53; I54; Q58; D60; I62; L63; I64; H69; A71; G73; L74; L76; V77; V82; N83; I84; I85; N88; L89; L90; I93 as major Protease Inhibitor resistance mutations;

T66; L74; E92; T97; E138; G140, Y143; S147; Q148; N155 as major Integrase Inhibitor resistance mutations;

G36; I37; V38; Q39; Q40; N42; N43 as major Entry Inhibitor resistance mutations; and combinations thereof.

Of note, particular sub-categories of mutant/resistant strains, including point mutations such as substitutions of one nucleotide with another, are known in the Art and are also considered by the invention.

Examples of drugs for which drug-resistant HIV strains have been found include: Zidovudine, Lamivudine, Emtricitabine, Didanosine, Stavudine, Abacavir, Zalcitabine, Tenofivir, Racivir, Amdoxovir, Apricitabine, Elvucitabine, Efavirenz, Nevirapine, Etravirine, Delavirdine, Rilpvirine, Tenofovir, Fosalvudine, Amprenavir, Tipranavir, Indinavir, Saquinavir, Fosamprenavir, Ritonavir, Darunavir, Atazanavir, Nelfinavir, Lopinavir, Raltegravir, Elvitegravir, Dolutegravir, Enfuvirtide, Maraviroc, Vicriviroc, and combinations thereof.

In particular, the HIV strain that is treated may be resistant to lamivudine (3TC), Tenofovir, Raltegravir, Zidovudine (AZT), Nevirapine (NVP), Efavirenz (EFV) and combinations thereof.

Uses and methods are both considered, in the sense of the invention.

Thus, the invention also relates to a method for treating or preventing a virus infection or virus-related condition in a patient, including HIV infection, consisting in administering to a patient in need thereof, an effective amount of the quinoline derivative of formula (1) as described above, wherein said method allows to maintain a low viral load after treatment termination.

Thus, the invention also relates to a method for treating or preventing a virus infection or virus-related condition in a patient, including HIV infection, consisting in administering to a patient in need thereof, an effective amount of the quinoline derivative of formula (1) as described above; and then terminating said treatment when: the viral load is low or undetectable; and/or the level of CD4+ cell count is maintained or restored.

Thus, the invention also relates to a method of treatment or prevention of a viral infection, in particular an HIV infection, consisting in administering to a patient for which an ineffectiveness or decline in a prior anti-viral (or anti-retroviral) treatment effectiveness has been stated, an effective amount of the quinoline derivative of formula (1) as described above.

Thus, the invention also relates to a method of treatment or prevention of a viral infection, in particular an HIV infection, consisting in administering to a patient infected by a drug-resistant strain, an effective amount of the quinoline derivative of formula (1) as described above.

According to some embodiments, the invention further relates to a method for treating an HIV infection or HIV-related condition in a patient, consisting of:

(i) administering to a patient in need thereof an effective amount of a quinoline derivative of formula (1) thereby treating the patient;

(ii) terminating the treatment;

(iii) optionally measuring the viral load and/or the CD4+ cell count in said patient after termination of treatment; wherein preferably:

a low or undetectable viral load is maintained; and/or a CD4+ cell count is stable or increased; after treatment termination;

(iv) optionally administering again to said patient in need thereof an effective amount of a quinoline derivative of formula (1) if the viral load is not low or undetectable and/or the CD4+ cell count is decreased.

A compound according to the present invention may be implemented within a pharmaceutical composition that may contain an effective amount of said compound, and one or more pharmaceutical excipients.

The aforementioned excipients are selected according to the dosage form and the desired mode of administration.

In this context they can be present in any pharmaceutical form which is suitable for enteral or parenteral administration, in association with appropriate excipients, for example in the form of plain or coated tablets, hard gelatine, soft shell capsules and other capsules, suppositories, or drinkable, such as suspensions, syrups, or injectable solutions or suspensions.

Any route of administration may be used. For example, the compound of formula (1) can be administered by oral, parenteral, intravenous, transdermal, intramuscular, rectal, sublingual, mucosal, nasal, or other means. In addition, the compound of formula (1) can be administered in a form of pharmaceutical composition and/or unit dosage form.

In particular, pharmaceutical compositions of the invention may be administered orally and/or parenterally.

According to one exemplary embodiment, pharmaceutical compositions of the invention may be administered orally.

Suitable dosage forms include, but are not limited to, capsules, tablets (including rapid dissolving and delayed release tablets), powder, syrups, oral suspensions and solutions for parenteral administration, and are more particularly capsules.

The pharmaceutical composition may also contain another drug for the treatment of HIV, well known to the man skilled in the art, in combination with a compound according to the present invention.

The following examples are provided as illustrations and in no way limit the scope of the present invention.

EXAMPLES

Example 1: Synthesis of Methyl 2,3,4-tri-O-acetyl-D-glucopyranosyluronate bromide-compound (3)

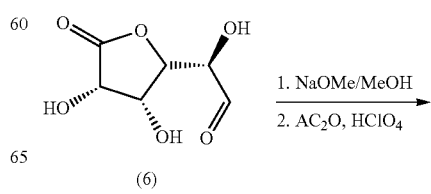

(6)

-continued

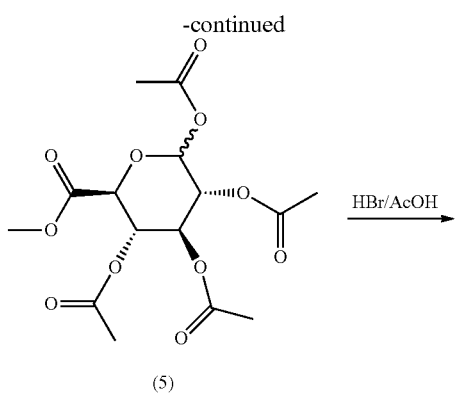

(5)

(3)

To commercially available D-glucurono-6,3-lactone compound (6) (48.6 g, 276 mmol), was added anhydrous methanol (500 mL) and Na metal (200 mg) at 0° C. The mixture was stirred under $N_2$ for 5 h. The solution was treated with Amberlite® IR-120 (Ir) resin until pH 3. After filtration the solvent was removed in vacuo to give a yellow gum. The residue was partially dissolved in $Ac_2O$ (100 mL), and a solution of $HClO_4$ (0.1 mL) in $Ac_2O$ (1 mL) was added dropwise to the reaction mixture at such a rate that the solution did not exceed 40° C. The reaction mixture was then stirred overnight at rt under $N_2$. The product was then dissolved in ethyl acetate, washed with 1 N HCl, $H_2O$, and brine, the organic phase was dried over $Na_2SO_4$.

The solvent was removed in vacuo to afford per-O-acetate intermediate compound (5) (96.5 g, 93%) as a white gum with an α/β ratio of 75:25. The spectroscopic data was consistent with previously reported spectroscopic data (1)

$^1$H NMR (400 MHz, $CDCl_3$): α-anomer 6.42 (d, 1H, J=3.9 Hz, 1H); 5.54 (dd, 1H, J, =10.0, $J_2$=9.7 Hz, 1H); 5.24 (dd, 1H, J, =10.2, $J_2$=9.7 Hz, 1H); 5.14 (dd, 1H, $J_1$=10.0, $J_2$=3.9 Hz, 1H); 4.43 (d, 1H, J=10.2 Hz, 1H); 3.77 (s, 3H, $CO_2$Me); 2.21, 2.06, 2.03 (3 s, 12H, 4 OAc).

$^1$H NMR (400 MHz, CDCl3): β-anomer 5.75 (d, 1H, J=7.8 Hz, 1H); 5.32-5.09 (m, 3H); 4.16 (d, 1H, J=9.3 Hz, H-5); 3.73 (s, 3H, $CO_2$Me); 2.10, 2.02, 2.01 (3 s, 12H, 4 OAc).

To per-O-acetate compound (5) obtained above (7.73 g, 20.54 mmol) under $N_2$ at 0° C. was added 45% HBr in acetic acid (25 mL) dropwise. The round bottom flask was placed inside a desiccator and stirred at 4° C. for 48 h. The mixture was diluted with ethyl acetate (100 mL), poured onto ice (50 g). The solution was washed with sat. aq. $NaHCO_3$ (50 mL), brine (50 mL), $H_2O$ (100 mL), the organic phase was dried over $Na_2SO_4$, filtered, and the solvent was removed in vacuo. The product was purified by flash chromatography (2:1 hexanes/ethyl acetate) to afford the glucuronosyl bromide compound (3) (3.50 g, 43%) as a pink gum. The $^1$H and $^{13}$C NMR spectra were consistent with literature data (Bollenback, G. N., Long, J. W., Benjamin, D. G., Lindquist, J. A., J. Am. Chem. Soc., 1955, 77, 3310).

$^1$H NMR (400 MHz, $CDCl_3$): 6.64 (d, J=4.1 Hz, 1H); 5.62 (dd, $J_1$=9.9, $J_2$=9.9 Hz, 1H); 5.25 (dd, J, =10.2, $J_2$=9.9 Hz, 1H); 4.86 (dd, J, =9.9, $J_2$=4.1 Hz, 1H); 4.59 (d, J=10.2 Hz, 1H); 3.77 (s, 3H, $CO_2$Me); 2.11, 2.06, 2.05 (3 s, 9H, 3 OAc).

Example 2: Production of Protected β-Glucuronides Compound (4)

To a solution of compound (2) (10 g, 25.72 mmol) in anhydrous toluene (300 ml) were added cadmium carbonate (2.6 g, 15.12 mmol), and the whole was refluxed with a dean stark trap for 12 hours. After cooling methyl α-acetobromoglucuronate III (10.3 g, 25.94 mmol) was added, and the whole was further refluxed for 24 hours. The precipitate was removed by filtration and washed with mixture of $CH_2Cl_2$/$CH_3OH$: 95/05. The filtrate and washings were combined and evaporated down. The oily residue was purified on Column chromatography on silica gel, eluting with $CH_2Cl_2$/MeOH: 98/02 to gave the protected Glucuronide compound (4) (3.5 g, 5.35 mmol) as a white foam.

$^1$H NMR (400 MHz, $CDCl_3$): 7.82 (d, J=9.2 Hz, 1H); 7.75 (dd, $J_1$=7.53 Hz, $J_2$=1.18 Hz, 1H); 7.56 (dd, $J_1$=8 Hz, $J_2$=1.18 Hz, 1H); 7.39 (d, J=8.43 Hz, 2H); 7.33 (d, J=8.43 Hz, 2H); 6.82 (d, J=8.1 Hz, 1H); 6.50 (d, J=8.65 Hz, 1H); 5.47 (t, J=9.44 Hz, 1H); 5.18 (t, J=9.44 Hz, 1H); 4.86 (m, 1H); 4.35 (d, J=10.20 Hz, 1H); 3.71 (s, 3H, $CO_2$Me); 2.05, 1.95, 1.94 (3 s, 9H, 3 OAc).

Example 3: Production of N-β-glucuronide of 8-chloro-N-(4-(trifluoromethoxy)phenyl)quinolin-2-amine Compound (1)

Hydrogen peroxide (30%, 10.4 ml) was added to a stirred suspension of lithium hydroxide monohydrate (4.73 g, 112 mmol) in water (44 ml), forming a solution within 3-4 minutes. The mixture was stirred for a further 10 min, and then added to a stirred solution of compound (4) (3.4 g, 5.2 mmol) in THF (140 ml). A precipitate formed within 15 min, and the mixture was quenched by addition of sodium thiosulfate after 75 min. the reaction being complete as judged by t.l.c. after 45 min. The mixture was acidified to pH 2.5 with 1M hydrochloric acid and crude product was extracted three times with ethyl acetate. The combined extracts were dried ($Na_2SO_4$) and solvent was removed under reduced pressure to leave chromatographically pure glucuronide 2 (2.5 g, 4.86 mmol, 93%) which was chromatographied to give yellow solid.

$^1$H NMR (400 MHz, DMSO-$D_6$): 8.07 (d, J=9.2 Hz, 1H); 7.81 (dd, $J_1$=8 Hz, $J_2$=0.9 Hz, 1H); 7.74 (dd, $J_1$=8 Hz, $J_2$=0.9 Hz, 1H); 7.56 (d, J=8.77 Hz, 2H); 7.52 (d, J=8.97 Hz, 2H); 7.28 (d, J=7.75 Hz, 1H); 6.50 (d, 1H, J=9.2 Hz, 1H); 6.34 (d, 1H, J=8.2 Hz, 1H); 5.17 (broad, 2H); 3.78 (d, 1H, J=9.4 Hz, 1H); 3.14-3.48 (m, 4H).

$^{13}$C NMR (133 MHz, DMSO-$D_6$): 171.25; 157.07; 148.08; 142.86; 138.91; 133.11; 130.27; 130.02; 127.38; 125.37; 123.66; 122.58; 121.84; 119.29; 112.47; 84.27; 78.32; 72.35; 70.18

Example 4: Compounds of Formula (1) and (2) Interact with the CBC Complex and Promote the Interaction of CBP20 with CBP80

1. Material & Methods
A. Preparation the recombinant CBC complex for in vitro studies.

The recombinant CBC complex, comprising CBP20 and CBP80, is prepared according to the protocol which has been described in Worch, R. et al. (Specificity of recognition of mRNA 5' cap by human nuclear cap-binding complex. RNA 11, 1355-1363 (2005)).

B. Labeling of Compound 1 with a Photoactivable Moiety and Induction of Dose-Dependent Covalent Bridging.

Compound 1 can make covalent binding with purified CBC complex after 15 min irradiation with UV light at 365 nm.

C. Gel-Mobility Shift Assay

Recombinant human CBC was incubated with a capped RNA substrate in the presence of increasing concentrations of compound 1 or compound 2 or a m(7)GpppG cap analogue and analyzed by native gel electrophoresis in order to resolve the different RNA and RNA-protein complexes according to Mazza et al. (Large-scale induced fit recognition of an m(7)GpppG cap analogue by the human nuclear cap-binding complex. EMBO J. 21, 5548-5557 (2002).

D. Limited Proteolysis on the CBC Complex.

Limited proteolysis of the CBC complex has been established according to the protocol described in Mazza et al. (Large-scale induced fit recognition of an m(7)GpppG cap analogue by the human nuclear cap-binding complex. EMBO J. 21, 5548-5557 (2002)).

E. Mass-Spectrometry Analysis.

Mass-spectrometry analysis of the CBC complex has been established according to the protocol described in Schirle et al. (Mass spectrometry-based proteomics in preclinical drug discovery. Chem Biol., 19:72-84 (2012)).

Proteins were separated on SDS-PAGE gels (4-15% polyacrylamide, Mini-PROTEAN® TGX™ Precast Gels, Bio-Rad, Hercules USA) and stained with Page Blue Stain (Fermentas). Gel lanes were cut into 3 gel pieces and destained with three washes in 50% acetonitrile and 50 mM TEABC (TriEthylAmmonium BiCarbonate). After protein reduction (with 10 mM dithiothreitol in 50 mM TEABC at 56° C. for 45 min) and alkylation (55 mM iodoacetamide TEABC at room temperature for 30 min) proteins were digested in-gel using trypsin (1 μg/band, Gold, Promega, Madison USA) as previously described in Shevchenko et al. (Mass spectrometric sequencing of proteins silver-stained polyacrylamide gels. Anal. Chem. 1996, 68 (5), 850-8; 1996). Digested products were dehydrated in a vacuum centrifuge and reduced to 4 μL.

Generated peptides were analyzed on-line using nanoflow HPLC-nano-electrospray ionization on a Q-Exactive mass spectrometer (ThermoScientific, Waltham USA) coupled with an Ultimate 3000 RSLC apparatus (Thermo Fisher Scientific). Desalting and pre-concentration of the samples were performed on-line on a Pepmap® precolumn (0.3 mm×10 mm). A gradient consisting of 0-55% B for 35 min and 90% B for 10 min (A=0.1% formic acid in water; B=0.1% formic acid, 80% acetonitrile in water) at 300 nl/min was used to elute peptides from the capillary (0.075 mm×150 mm) reverse-phase column (Acclaim PepMap® RSLC, Thermo Fisher Scientific), fitted with an uncoated silica PicoTip Emitter (NewOjective, Woburn, USA). Eluted peptides were electrosprayed online at a voltage of 1.9 kV into an Q-Exactive mass spectrometer. MS spectra (m/z, 400-2,000) were acquired using the Xcalibur software (v 3.0, Thermo Fisher Scientific) in the positive ion mode with a resolution of 70,000 for the precursor ion scan. For all full scan measurements with the Orbitrap detector a lock-mass ion from ambient air (m/z 445.120024) was used as an internal calibrant as described in Olsen et al. (Parts per million mass accuracy on an Orbitrap mass spectrometer via lock mass injection into a C-trap. Mol. Cell. Proteomics 4, 2010-2021; 2005). MS/MS spectra were acquired in the Data-Dependent Acquisition mode, in which the TOP10 most abundant precursor ions with maximum integration time of 250 ms and a target value of $3*10^6$ ions. Peptide fragmentation was performed via higher-energy collisional dissociation set at 26 V of normalized collisional energy. The MS/MS spectra were acquired at a resolution of 17,500, with a target value of $1*10^5$ ions and a maximum integration time of 120 ms.

All MS/MS spectra were searched against the homo sapiens CPS database (85,895 sequences and specific sequences of CBP80-CBC20, release September 2014, http://www.uniprot.org/) by using the Proteome Discoverer software v1.4 (Thermo Fisher Scientific) and Mascot v2.5 algorithm (http://www.matrixscience.com/) with trypsin enzyme specificity and one trypsin missed cleavage. Carbamidomethylation was set as fixed cystein modification and oxidation was set as variable methionine modification for searches. Mass tolerances in MS and MS/MS were set to 5 ppm and 0.5 Da respectively. Management and validation of mass spectrometry data were performed using the Proteome Discoverer software (Mascot significance threshold p<0.05, with a minimum of one peptide per protein).

In addition to protein/peptide identifications, the Skyline software v2.6. (http://proteome.gs.washington.edu/software/skyline) was used to process ion intensity chromatograms of specific peptides from full-scan mass spectral data (MS1) acquired during HPLC MS/MS proteomic experiments, as described in MacLean et al. (Effect of collision energy optimization on the measurement of peptides by selected reaction monitoring (SRM) mass spectrometry. Anal Chem 82, 10116-10124; 2010).

2. Results

Using a derivative of Compound 2 that has a photoactivatable moiety and competition with Compound 2 on purified recombinant CBP20 and CBP80 (CBC), we discovered that Compound 2, itself, is able to induce dose-dependent covalent bridging between CBP20 and CBP80, after UV irradiation and this complex can be resolved by SDS-PAGE. The same results were obtained with the glucuronidated Compound 1, the more soluble derivative of Compound 2 that is produced as metabolite using human hepatocytes.

Mass spectrometry analysis of gel purified CBP20, CBP80 and the CBC complex (80 and 20), showed that the trypsin digestion of CBC (CBP80 and CBP20) complex gave rise to all predicted peptides except the peptide at the position 37-66 of CBP20 which was reproducibly under-represented or absent. However, individual digestion with trypsin of either CBP20 or CBP80 from the same sample gave rise to all predicted peptides. Remarkably, the peptide 37-66 in the crystal structure of the CBC (Mazza et al.; Crystal structure of the human nuclear cap binding complex. Mol. Cell 8, 383-396 (2001)) corresponds to the interface between CBP20 and CBP80, which could be the site of interaction between Compound 2 and the CBC.

However, neither Compound 2 nor its metabolite Compound 1 affected the binding of CBC complex to capped RNA probe in a gel mobility shift assay. While the complex between CBC and capped RNA was competed by the $m^7$GpppG, no competition was observed with Compound 1 or 2 at any concentration tested, confirming that both Compounds do not interact with the cap binding site of CBP20 (FIGS. 1A and 1B).

Those results thus fully support a common mechanism of action between Compound 1 and 2. Those results also support that both Compounds bind directly to the CBC complex but do not interfere with cap binding nor export of bulk pol II transcripts, while preventing the export of viral RNA, including Rev-mediated export of viral RNA.

Example 5: Potency of Compounds 1 to Inhibit HIV-1 Production in Macrophages-Infected Cells 1. Material & Methods A. Cell Culture and Infection Buffy coats from HIV-negative individuals were obtained from the local blood donation center in Zurich, Switzerland (http://www.blutspendezurich.ch/) and Centre de transfusion sanguine Montpellier. Human peripheral blood mononuclear cells (PBMCs) were isolated by Ficoll (Axis-Shield PoC AS) gradient centrifugation. The cells have then been cultivated at 37° C., 5% CO2 to a density of $1\times10^6$ cells/mL in RPMI Glutamax medium (Life Technologies Ref 61870-010) supplemented with 10% fetal calf serum (FCS) (Thermo Fischer Ref SV30160.03), 1000 U/mL of IL2 (Peprotech Ref 200-02) and 5 µg/mL of PHA (Roche Ref 1249738) for activation. Three days later, cells have been pooled and resuspended to a density of $1\times10^6$ cells/mL in RPMI Glutamax medium supplemented with 10% fetal calf serum (FCS) 1000 U/mL of IL-2 for infection. HIV-1 infection has been performed with 10 µg of Ada-M R5 HIV strain per mL of cells for 4 hours. Cells were then centrifuged and resuspended to a density of $1\times10^6$ cells/mL in medium supplemented with diluted DMSO solubilized drug (Sigma Ref D4818) according to a final 0.05% DMSO concentration. Cells were treated for 6 days with a partial medium change at day 3. Cell culture supernatant HIV p24 titration was performed by ELISA with Ingen Innotest kit (Ingen Ref 80564) according to manufacturer's instructions.

To generate monocyte derived macrophages (MDMs), monocytes were isolated using CD14 microbeads (catalog no. 130-050-201; Miltenyi) and cultured in X-VIVO10 medium (Lonza) supplemented with GM-CSF 1000 U/ml and M-CSF 100 ng/ml for 6 days. Monocytes were seeded at a cell count of 50'000 cells per well in a 96 well plate. After 6 days medium was replaced with X-VIVO10 w/o Cytokines. After 2 days Macrophages were treated with Compound (1) o/n and next day infected with Yu-2 virus for 6 hrs, washed with PBS and cultured in medium containing the compounds for 12 days. Supernatant for p24 Elisa was collected 2 times a week.

2. Results

FIG. 2 illustrates the results. The graph at the bottom and on the right gathers the results of the other three graphs. "Cpd (1)", means compound of formula (1).

Cells were treated with 1.5 µM up to 30 µM and p24 antigen levels were monitored in culture supernatant over a 12 day period (R-10 corresponds to untreated cells) (FIG. 2). Interestingly, Compound (1) blocked virus replication efficiently and in a dose dependent manner reaching inhibition levels of up to 60% in primary macrophages at 30 µM.

Those results provide evidence that compound (1) of the invention has low toxicity, but remain suitable for inhibiting HIV-1 replication, in macrophages.

Example 6: Pharmacokinetic (PK) Parameters of Compound (1) after a Single Oral Administration of Compound (2)

1. Material & Methods 1.1 Group of Patients

The present document details the pharmacokinetic (PK) results obtained in a first-in-man study with compound (2) consisting in a single oral ascending dose in healthy male subjects. Four (4) dose levels were investigated (50, 100, 150, and 200 mg).

At each dose level, 6 subjects were included and received a single oral dose of compound (2) so that a total of 24 subjects participated to the study and completed it. No study deviation was identified at the time of the PK analysis and thus, all subjects were included in the PK analysis.

In this study, plasma levels of compound (1) were measured.

PK blood sampling was initially defined up to 48 h post-dose. Further to first results after single oral administration of 50 mg compound (2) showing that compound (1) exhibited a long terminal half-life ($t_{1/2}$), it was decided to increase the PK follow-up by adding 3 blood samples collected up to 45 days after compound (2) administration.

Blood samples for assessment of compound (1) plasma levels are scheduled at the following time points:

Day 1 pre-dose, 0.33, 0.66, 1.00, 1.50, 2.00, 2.50, 3.00, 4.00, 6.00, 8.00, 10.00, and 12.00 h post-dose;
Day 2 24.00 and 36.00 h post-dose;
Day 3 48.00 h post-dose;
Day 10 240 h post-dose;
Day 24 576 h post-dose;
Day 45 1080 h post-dose.

1.2 Pharmacokinetics

Plasma concentrations were processed throughout the PK software for PK data generation. The PK parameters were calculated by non-compartmental analysis (NCA), using Phoenix® WinNonlin® (Pharsight Corporation) running on a personal computer.

For the calculation of the PK parameters and characteristics the following rules were applied:

All the plasma concentrations validated provided to the pharmacokineticist were used for the PK analysis.

The actual blood sampling time points related to the preceding administration was used.

At time points in the lag-time between time zero and the first concentration equal or above limit of quantification (LOQ), concentrations below LOQ were set to zero (0). Concentrations below limit of quantification (BLOQ) between 2 concentrations equal or above LOQ were considered as missing data. Trailing concentrations BLOQ were used in calculations.

If pre-dose concentration was missing, it was arbitrary set to zero (0) assuming that expected results would have been BLOQ.

For each subject receiving the active treatment in each cohort, the following PK parameters of compound (1) were to be derived:

$C_{max}$ The observed maximum concentration measured in plasma was obtained directly from the concentration-time data.

$t_{max}$ The time at which $C_{max}$ was apparent, identified by inspection of the plasma drug concentration vs. time data by Phoenix® WinNonlin®.

$AUC_{0-t}$ The area under the concentration-time curve from time zero (pre-dose) to the time of last quantifiable concentration was calculated using a linear trapezoidal method.

ke The terminal plasma elimination rate-constant was estimated from log-linear regression analysis of the terminal phase of the plasma concentration-time profile. The number of points included in the terminal phase was determined by visual inspection of the semi-log plots of the plasma concentration-time profiles (at least 3).

$AUC_{0-\infty}$ The AUC from time 0 to infinity was calculated as $AUC_{0-\infty}=AUC_{0-t}+AUC_{t-\infty}$, where $AUC_{0-t}$ is the area under the concentration-time curve from time zero (pre-dose) to the time of last quantifiable concentration calculated using a log-linear trapezoidal method and $AUC_{t-\infty}=C_t/ke$, where $C_t$ is the measured concentration at time of the last quantifiable concentration t. The extrapolated part of $AUC_{0-\infty}$ must be <20% for the value to be considered as reliable.

$t_{1/2}$ The apparent terminal elimination half-life was calculated as ln 2/ke, where ke is the elimination rate constant during the terminal phase determined by the log-linear regression obtained on at least the 3 last quantifiable concentrations and using actual blood sampling times. The correlation coefficient for the goodness of the fit of the regression line through the data points must be 0.8500 or higher, for the value to be considered reliable.

2. Results

After single oral administration of compound (2), regardless of the dose, biotransformation of compound (2) into compound (1) is fast and appears as a major drug metabolism since compound (1) plasma concentrations are markedly higher than those of the parent drug. First quantifiable compound (1) concentration is generally observed at 40 min post-dose (20 subjects out of 24), earlier in one case (20 min post-dose for Subject No. 306) and later in 3 cases (1 h post-dose for Subject No. 102, No. 106, and No. 406).

Then, plasma concentrations increase up to $C_{max}$ generally occurring at 4 h post-dose (⅔ of the subjects) but ranging from 3 h post-dose (2 cases) to 6.00 h post-dose (6 cases). Decrease of compound (1) plasma concentrations is slow and can be followed up to 24 to 45 days after drug administration.

In all cases, PK values are determined with a very good accuracy and extrapolated Area Under the Curve (AUC) was very limited, therefore all PK parameters of all subjects are reliable and used for further statistics assessment.

Individual plasma concentrations are presented by dose level. Descriptive statistics for the plasma concentrations are presented as mean and standard deviation (SD) and calculated if at least ⅔ (i.e., 4 out of 6) of the plasma values per time-point were above Limit of Quantification (LOQ).

Descriptive statistics of the PK parameters were presented as arithmetic mean, SD, coefficient of variation (CV %), median, minimum (Min) and maximum (Max) values, and geometric mean (GM).

Descriptive statistics of derived pharmacokinetic (PK) parameters of compound (1) after single oral administration of 50 to 200 mg of compound (2) are summarized herebelow, in Table 1.

TABLE 1 summary of descriptive statistics of compound (1) PK parameters after single oral administration of 50 to 200 mg of compound (2)

| Dose (mg) | | $C_{max}$ (ng/mL) | $t_{max}$ (h) | $AUC_{0-t}$ (ng · h/mL) | $AUC_{0-\infty}$ (ng · h/mL) | $t_{1/2}$ (h) |
|---|---|---|---|---|---|---|
| 50 | N | 6 | 6 | 6 | 6 | 6 |
| | Mean | 2626.67 | 4.00 | 208810.90 | 211777.45 | 97.30 |
| | SD | 754.26 | 4.00-4.00 | 86272.80 | 90391.66 | 19.96 |
| | GM | 2536.08 | — | 196037.86 | 198171.39 | 95.69 |
| 100 | N | 6 | 6 | 6 | 6 | 6 |
| | Mean | 5716.67 | 4.00 | 498879.23 | 505290.05 | 111.30 |
| | SD | 2150.08 | 4.00-6.00 | 206400.78 | 203392.76 | 10.81 |
| | GM | 5403.19 | — | 467828.81 | 475563.80 | 110.85 |
| 150 | N | 6 | 6 | 6 | 6 | 6 |
| | Mean | 9243.33 | 4.00 | 659186.04 | 664063.50 | 99.18 |
| | SD | 4622.37 | 3.00-4.00 | 398823.55 | 401716.80 | 28.24 |
| | GM | 8272.56 | — | 559712.00 | 563290.73 | 95.70 |

TABLE 1-continued summary of descriptive statistics of compound (1) PK parameters after single oral administration of 50 to 200 mg of compound (2)

| Dose (mg) | | $C_{max}$ (ng/mL) | $t_{max}$ (h) | $AUC_{0-t}$ (ng · h/mL) | $AUC_{0-\infty}$ (ng · h/mL) | $t_{1/2}$ (h) |
|---|---|---|---|---|---|---|
| 200 | N | 6 | 6 | 6 | 6 | 6 |
| | Mean | 7906.67 | 6.00 | 558711.56 | 560431.14 | 89.55 |
| | SD | 6167.27 | 4.00-6.00 | 395064.74 | 396155.03 | 19.17 |
| | GM | 5895.95 | — | 436350.02 | 438116.45 | 87.81 |

* median and range (Min-Max)

Median $t_{max}$ was comparable across dose levels varying from 4 to 6 h post-dose with a very low inter-individual variability.

Inter-individual variability of $C_{max}$ and AUCs tended to increase with compound (2) doses, being below 50% for the 2 lower dose levels and reaching 70 to 80% at 200 mg. One can note that $C_{max}$ and AUCs values were within the same range for Subjects of the 200 mg cohort.

The $t_{1/2}$ of compound (1) was roughly comparable in terms of mean values and variability from 50 to 200 mg was between 90 and 110 h.

The invention claimed is:

1. A quinoline derivative of formula (1)

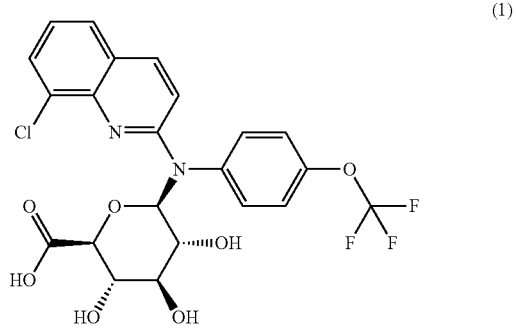 [SMILES: O=C(O)[C@H]1O[C@@H](N(c2ccc(OC(F)(F)F)cc2)c2ccc3cccc(Cl)c3n2)[C@H](O)[C@@H](O)[C@@H]1O]

(1)

or a pharmaceutically acceptable salt thereof.

2. A pharmaceutical composition comprising the quinoline derivative according to claim 1 and at least one pharmaceutically acceptable excipient.

3. A medicament comprising the quinoline derivative according to claim 1.

4. A process for preparing a quinoline derivative, comprising a step of treating compound (4)

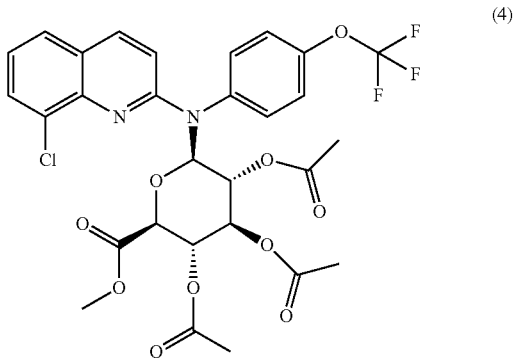 [SMILES: COC(=O)[C@H]1O[C@@H](N(c2ccc(OC(F)(F)F)cc2)c2ccc3cccc(Cl)c3n2)[C@H](OC(C)=O)[C@@H](OC(C)=O)[C@@H]1OC(C)=O]

(4)

in a solution of lithium hydroperoxide, thereby forming a quinoline derivative of formula (1)

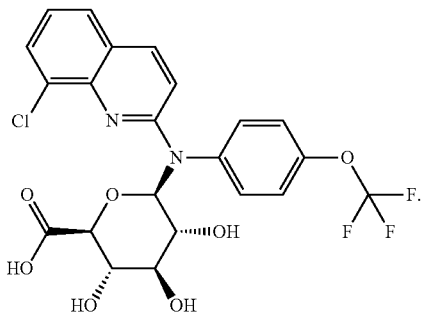

5. The process of claim 4, wherein, before treating compound (4) in a solution of lithium hydroperoxide, reacting formula (2)

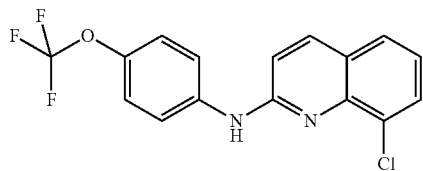 [SMILES: FC(F)(F)Oc1ccc(Nc2ccc3cccc(Cl)c3n2)cc1]

with a compound of formula (3):

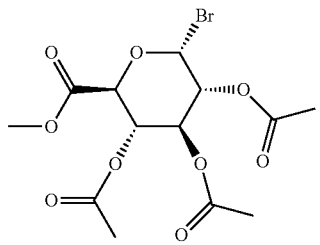

in the presence of a heavy metal salt and solvent thereby forming compound (4).

6. A compound of formula (4)

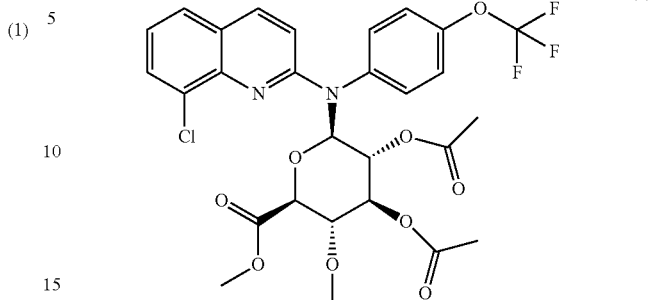

or a pharmaceutically acceptable salt thereof.

7. A method for treating or reducing likelihood of occurrence or re-occurrence, of a human immunodeficiency virus (HIV) infection or of acquired immune deficiency (AIDS), comprising administering to a subject a quinoline derivative of formula (1)

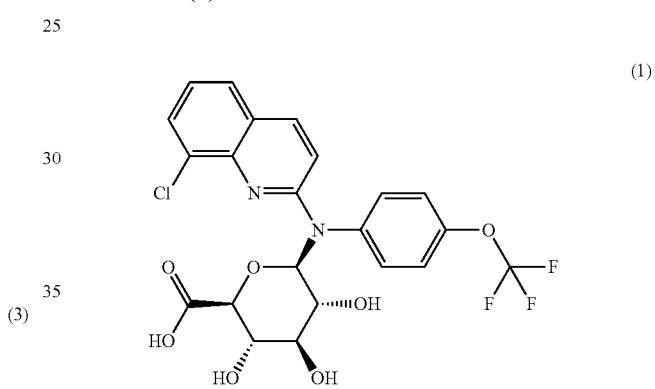

or a pharmaceutically acceptable salt thereof.

8. The method of claim 7, wherein the method is for treating AIDS.

9. The method of claim 7, wherein the method is for treating a HIV infection.

10. The method of claim 7, wherein the method is for treating a human immunodeficiency virus (HIV) infection, or AIDS.

* * * * *